United States Patent
Hale et al.

(10) Patent No.: US 6,623,976 B1
(45) Date of Patent: Sep. 23, 2003

(54) COMBUSTIBILITY MONITOR AND MONITORING METHOD

(75) Inventors: John Martin Hale, Cyprus, CA (US); Gerard Roland Stehle, Machilly (FR); Dominique Serratore, Geneva (CH); Eugen Weber, deceased, late of Hinwil (CH), by Peter Weber and André Weber, heirs

(73) Assignee: Orbsphere Laboratories Neuchatel SA, Neuchatel (CH)

( * ) Notice: Subject to any disclaimer, the term of this patent is extended or adjusted under 35 U.S.C. 154(b) by 0 days.

(21) Appl. No.: 09/284,849

(22) PCT Filed: Oct. 16, 1997

(86) PCT No.: PCT/EP97/05714
§ 371 (c)(1),
(2), (4) Date: May 8, 2000

(87) PCT Pub. No.: WO98/18001
PCT Pub. Date: Apr. 30, 1998

(51) Int. Cl.$^7$ .............................................. G01N 25/26
(52) U.S. Cl. ..................... 436/160; 436/155; 374/37; 73/432; 73/36; 73/26; 73/25; 73/35
(58) Field of Search .................... 436/160, 155; 374/37; 73/432, 36, 26, 35, 25

(56) References Cited

U.S. PATENT DOCUMENTS

| | | | | |
|---|---|---|---|---|
| 2,939,312 A | * | 6/1960 | Jacobs et al. .................. | 73/36 |
| 3,186,213 A | * | 6/1965 | Donnell .......................... | 73/36 |
| 3,768,313 A | * | 10/1973 | Jahansson et al. ............ | 73/432 |
| 4,140,004 A | | 2/1979 | Smith et al. | |
| 4,351,614 A | * | 9/1982 | Garnier ........................ | 374/37 |

FOREIGN PATENT DOCUMENTS

| | | |
|---|---|---|
| EP | 0 531 614 A | 3/1993 |
| FR | 2 542 090 A | 9/1984 |

OTHER PUBLICATIONS

Database WPI Week 8128 Derwent publications Ltd., London, GB; An 81–50929d '28! XP–002057301.
JP 56 025 988 B (Yokogawa Electric Works Ltd), 1981.

* cited by examiner

Primary Examiner—Jill Warden
Assistant Examiner—Brian Sines
(74) Attorney, Agent, or Firm—Blank Rome Comisky & McCauley LLP

(57) ABSTRACT

An apparatus (1) for determining the concentration of a critical first component, such as hydrogen, of an atmosphere or environment (E), wherein the first component is capable of forming a combustible mixture with a second component, such as oxygen; the apparatus comprises: (A) a sampling unit (10) including: (A1) a small measuring chamber (12) operatively connected with an ignition means (135) capable of being operated so as to initiate in said chamber a combustion of said critical first component by reaction with said second component, and (A2) at least one sensor (15) operatively connected with said measuring chamber for generating a signal formed by essentially proportionate contributions from all significant components contained in said measuring chamber; (B) at least one flame arrestor (14) intervening between said measuring chamber (12) and aid environment (E) of interest; and (C) a control unit (16) capable of imposing a mode of operation in at least two distinct phases wherein, during a first phase, said environment of interest is allowed to accumulate in said measuring chamber; and wherein, during a second phase, said ignition means is operated for initiating said combustion in said chamber; and (D) a means (17) for evaluating at least one signal generated by said at least one sensor before operation of said ignition means, and at least one signal generated by said at least one sensor after operation of said ignition means so as to generate a signal (S) which is indicative of said concentration of said critical first component in said environment of interest.

21 Claims, 4 Drawing Sheets

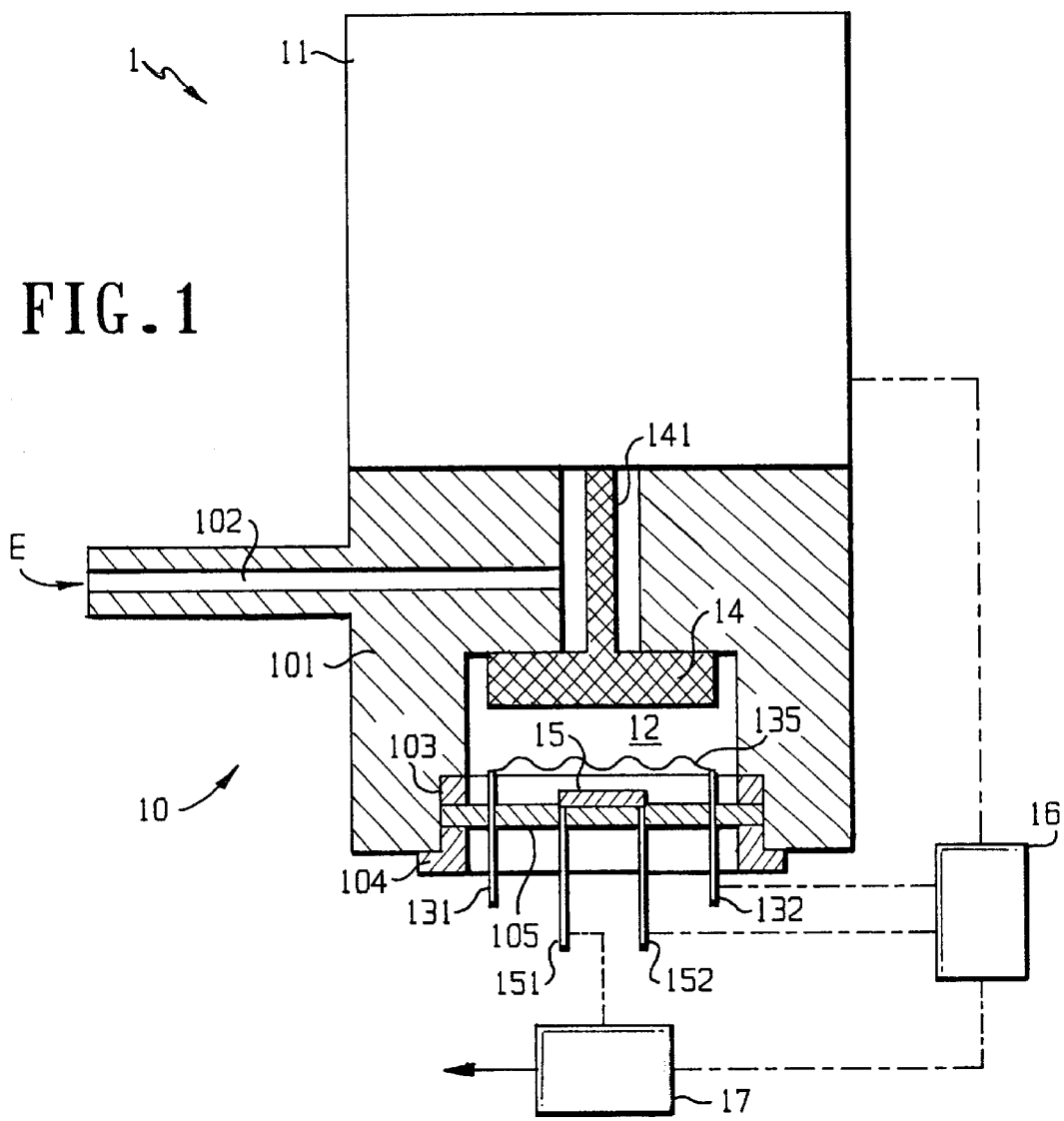

COMBUSTIBILITY MONITOR AND MONITORING METHOD

FIELD OF THE INVENTION

The present invention generally relates to analysis of potentially hazardous mixtures of substances and specifically to apparatus and method means for combustibility monitoring by determining the concentration of a first critical component in an environment or atmosphere of interest containing a second component that is capable of forming a combustible mixture with the critical first component. The invention is of particular relevance for monitoring gaseous substances and atmospheres containing them.

Combustible gaseous mixtures are those in which a first gaseous component thereof is capable of rapid exothermic reaction with a second component of the mixture by an oxidative process which may, but need not, involve oxygen as the oxidizing agent. Depending upon the relative amounts of the reacting components, the speed of reactions, the amount of heat generated, and the activation required for initiation of the reaction, such mixtures may cause substantial hazards.

Consequently, prevention of the formation of such mixtures, such as by continuous monitoring of an atmosphere of interest, is of general technological importance, and may be mandatory by law. Such monitoring is of particular importance in substantially enclosed environments, such as housings of processors which generate combustible or explosive gas mixtures by evolving hydrogen, possibly but not necessarily in the presence of a surplus of oxygen, or other relatively enclosed spaces where hazardous or potentially hazardous gas mixtures may occur without human intervention, such as methane in the air of mines, or spaces in areas where gaseous combustible chemicals or fuels are produced, processed, distributed or consumed.

The presence of elemental hydrogen in an atmosphere that contains, or may come into contact with, a sufficient amount of oxygen, such as air, is particularly hazardous because of the extremely high specific amount of heat generated upon reaction between hydrogen and oxygen and the extremely low activation energy required for initiation of the reaction. Thus, hydrogen monitoring is needed in various industrial work-places, e.g. in the immediate vicinities of containers deliberately filled with gaseous hydrogen, such as large electrical transformers and nuclear or chemical reactors as well fuel reservoirs whenever liquid or gaseous hydrogen is used as a fuel. The atmosphere within such containers or a surrounding enclosure will become explosive when the amount of gaseous hydrogen as the first component attains 5%, by volume, if oxygen as the second component is present in an at least stoichiometrically equivalent amount or in stoichiometric excess, or when at least 5%, by volume, of gaseous oxygen as the first component is formed in the presence of a stoichiometric equivalent or excess of gaseous hydrogen as the second component.

However, while monitoring of atmospheres of interest that do contain oxygen and may contain hydrogen is of particular interest, the present invention is not limited to this aspect but is applicable wherever a first component (which may be an oxidizable or an oxidizing compound) is capable of forming a "combustible" i.e. exothermally reactive mixture with a second component which provides the complement of the reaction, i.e. is oxidizing for an oxidizable first component, or—in reverse—is oxidizable by an oxidizing first component. While elemental oxygen is a typical "second" component because of its universal appearance in air, other oxidizing substances, notably those having a normally (i.e. under normal conditions of temperature and pressure) gaseous phase, such as fluorine or bromine, are capable of forming exothermally reactive gaseous mixtures with such oxidizable gases as hydrogen as well. Accordingly, the term "combustion" is neither to be understood as a limitation to reactions involving oxygen as the oxidizing component, nor as a limitation to monitoring of oxidizable components of mixtures.

Consequently, the term "critical first component" as used herein is intended to refer generally to that particular and potentially appearing component of an environment or atmosphere of interest which is monitored so as to indicate formation of a combustible mixture with a second component which may be but need not be present in the environment of interest.

Examples of oxidizable and typically gaseous substances of particular interest herein other than hydrogen are low molecular hydrocarbons (methane, ethane, propane, butane, singly or in mixtures) as well as other organic or inorganic substances including low boiling organic compounds, cyanogen, carbon monoxide, hydrogen sulfide etc., which can form combustible mixtures with a reactively complemental component, such as typically oxygen, capable of fast or "explosive" reaction.

The concentrations, or concentration limits, at or within which a given pair of an oxidizable and an oxidizing component forms an explosive mixture are known in the art of chemical processing and do not require specific explanation herein.

PRIOR ART

Various apparatus and method means for determining the concentration of a component of a gaseous mixture are known and operate on various principles of detection, including measurement of thermal conductivity, measurement of the heat of combustion by calorimetry using, for example, a pellistor, determination of oxidizable components of an atmosphere, and methods based on the modification of electrical conductivity of semiconductors caused by the electron donating properties of oxidizable substances, cf. EP-A-0 429 397 or EP-A-0 607 756 and the literature cited therein; such prior art means could, in theory, be used for monitoring of combustible atmospheres.

However, such prior art methods have not proved to be entirely satisfactory for monitoring potentially combustible atmospheres; disadvantages include inherent difficulties of avoiding the risk of igniting the atmosphere of interest, sensitivity to interference by oxygen or other impurities, notably when electrochemical methods or the use of semiconductor are concerned, as well as insufficient stability of the monitored parameters, or lack of precision and/ reproducibility and, hence, poor reliability.

Prior art amperometric means for measuring elemental gaseous hydrogen are disclosed, e.g. in U.S. Pat. No. 4,563, 249. Continuous monitoring of potentially hazardous hydrogen/oxygen mixtures as disclosed, for example, in U.S. Pat. Nos. 4,906,339 and 4,985,130 operates on the principle of selectively measuring the concentration of either component in the presence of the other and could indicate the formation of an explosive mixture. Electrolytes are required in these methods, however, and if the electrolyte is aqueous, prolonged operation in a dry gaseous environment causes evaporation of water and requires frequent replacement of the electrolyte and precludes unattended operation for prolonged periods of time; non-aqueous electrolytes, on the other hand, are not satisfactory because they cause a rapid drift of the monitoring signal.

Non-amperometric monitoring methods and apparatus such as disclosed in U.S. Pat. Nos. 5,144,831 and 5,255,553 (also termed pulse monitoring herein) while capable of monitoring various substances that were difficult to monitor by prior art methods are operable with binary—or at least pseudo-binary-mixtures and become less reliable when the substance to be monitored is accompanied by interfering components.

OBJECTS AND SUMMARY OF THE INVENTION

Accordingly, a first general object of the present invention are apparatus and method means for monitoring potentially explosive environments (including atmospheres within an essentially enclosed space) while avoiding or minimizing the above mentioned disadvantages of prior art, yet providing economic and completely safe apparatus and method means for continuously analyzing or monitoring mixtures that are potentially WO-A-9 602 826 discloses a device and method for measuring the amount of a reactive gaseous component in a gas or gas mixture contained within a voluminous enclosed space containing a catalyst capable of exothermally reacting with the gas of interest and measuring the heat generated by the catalytically induced reaction of the reactive gaseous component. The rate of combustion is that of a catalytically induced reaction and does not approach explosive combustion initiated by ignition of an explosive gas mixture. In fact, such explosive combustion would neither be practical in a voluminous chamber nor yield any significant data.

GB-A-1 427 515 discloses a device and a method based on a similar concept of a catalytically induced reaction caused by a catalyst arranged within a voluminous space and containing an embedded thermometer element for measuring any temperature caused by reaction of the gas of interest with catalyst. Again, explosive combustion would not be practical nor yield any significant data.

Accordingly, a first object of the invention is an improved method of monitoring potentially explosive environments (including atmospheres within an essentially enclosed space) avoiding the disadvantages of prior art and provide for a reliable and safe test for explosive combustibility of a gas mixture by actually attempting rapid, i.e. explosive combustion in a continuous sequence of test and measuring cycles, each cycle including an actual ignition, and measuring the composition of the gas sample before and after ignition because any combustion of this type will have a most distinct impact upon the composition of the gas mixture contained in the measuring chamber so as to yield reliable and significant data, providing apparatus and method means for continuously analyzing or monitoring gaseous mixtures that are potentially or actually hazardous because of their propensity for very rapid and, sometimes, virtually spontaneous combustion, and which suffer no interference from humidity, nor the presence of oxygen or other impurities typical for a specific field of application.

A further object of the invention are apparatus and method means for analysis of gas mixtures by thermal conductivity monitoring, said mixtures containing a combustible component in the presence of at least one other substance which might interfere with the chosen method of analysis, and in the presence of non-interfering other substances, wherein measurement is effected according to the pulsing method specified in more detail below.

These and further objects and advantages as will become apparent from the following specification are achieved, according to a first embodiment of the present invention, by an apparatus for determining the concentration of a critical first component, such as hydrogen, of an environment, when the first component is capable of forming a combustible mixture with a second component, such as oxygen; said apparatus comprising:

(A) a sampling unit including:
   (A1) a small measuring chamber operatively connected with an ignition means capable of being operated so as to initiate in said chamber a combustion of the critical first component by reaction with the second component, and
   (A2) at least one sensor operatively connected with the measuring chamber for generating a signal formed by essentially proportionate contributions from all significant (i.e. contributing to the measurable parameters of interest) components contained in the measuring chamber;
(B) at least one flame arrestor positioned between the measuring chamber and the environment or atmosphere of interest; and
(C) a control unit capable or imposing a mode of operation in at least two distinct phases wherein, during a first phase, the environment or atmosphere of interest is allowed to accumulate in the measuring chamber; and wherein, during a second phase, the ignition means is operated for initiating combustion in the chamber; and
(D) a means for evaluating at least one signal generated by the at least one sensor before operation of the ignition means, and at least one signal generated by the at least one sensor after operation of the ignition means so as to generate a signal which is indicative of the concentration of the critical first component in the environment or atmosphere of interest.

The apparatus may include means (E) for cyclically flushing the chamber with a gas, such as air, which is free of the critical first component but may contain the second component, such as oxygen. In other words, the second component required for explosive combustion of the first component may be—but need not be—contained in the environment of interest.

According to a second preferred embodiment the invention provides for a method of determining the concentration of a critical first component of an environment or atmosphere of interest, said first component being capable of forming a combustible mixture with a second component; the method according to the invention comprises:

(a) providing a small receiving volume in operative connection with an ignition means capable of initiating combustion, in the receiving volume, of a mixture containing the critical first component and the second component;
(b) providing means between the receiving volume and the environment or atmosphere of interest so as to prevent that combustion within the receiving volume will initiate combustion outside the receiving volume and in the environment or atmosphere of interest;
(c) permitting, during a sampling phase, a portion of the environment or atmosphere of interest to enter into the receiving volume;
(d) providing at least one sensor in operative connection with the receiving volume so as to generate signals formed by essentially proportionate contributions from all significant components contained in the receiving volume;

(e) operating the ignition means so as to initiate combustion of the mixture of the first and the second component in the receiving volume;

(f) obtaining from the at least one sensor at least one signal before, and at least one signal after, operating the ignition means; and (g) processing the signals obtained before and after operation of the ignition means to generate a signal which is indicative off the concentration of the critical first component in the environment or atmosphere of interest.

The method according to the invention may include the additional step of flushing the receiving volume with a gas, such as air, which is substantially free of the critical first component, such as hydrogen.

The term "essentially proportionate contributions" with reference to the response of the at least one sensor is intended to indicate that the contribution of each component of the mixture in the measuring chamber should be proportionate to the relative amounts of the components. Preferably, the contributions are additive, and it is even more preferred if such contributions are linearly additive. The preferred sensors disclosed herein satisfy this requirement. Generally, monitoring according to the invention is effected in a prolonged if not "endless" sequence of cycles, each of which includes at least two-phases, i.e. before and after each operation of the ignition means, and such cycles will be repeated as long as the monitoring process is to be continued. Cycling times can be chosen as appropriate for a given purpose; typical cycling times may be in the range of from 1 second or less to 1 minute or more, neither limit being considered to be critical except that the response or sensitivity of the monitoring operation may suffer if cycling times are excessive. Each cycle may, however, include one or more additional phases as will be explained in more detail below.

The term "in operative connection" is intended to refer either to direct connection, e.g. the ignition means or sensor is arranged within the measuring chamber, or receiving volume, or is connected therewith, e.g. by a conduit. In a similar manner, the measuring chamber may be positioned within the atmosphere of interest, or be connected therewith by way of one or more conduits.

The term "small" with reference to the measuring chamber of the apparatus according to the invention, or with reference to the volume of the receiving space used in the inventive method, is intended to refer to a volume of the chamber or receiving space that is substantially negligible in relation to the volume of the environment or atmosphere of interest outside of, or connected with, the measuring chamber or receiving space. In absolute terms, a typical measuring chamber or receiving space according to the invention has a volume of less than 1 ml, typically about 0.1 ml. so as to minimize the quantity of energy released by combustion of the mixture of reactive components in the measuring chamber or receiving space.

Typically, the volume of the environment or atmosphere of interest is substantially greater, say, by more than two magnitudes than the volume of the chamber or receiving space, or, in reverse, the measuring chamber or receiving volume typically will be smaller than 1%, preferably lower than 0.1% of the volume of the atmosphere of interest.

PREFERRED EMBODIMENTS OF THE INVENTION

The measuring chamber, or the walling which encompasses the receiving volume, preferably is made of a material that under operating conditions is essentially inert, both physically and chemically, and—preferably—has a high thermal capacity such as typically stainless steel. Accordingly, stainless steel is a preferred but not limiting example of a material forming the measuring chamber or surrounding the receiving volume.

Generally, the parameters of the measuring chamber or receiving volume should be selected such that a temperature rise caused by combustion of the mixture of reactive components contained in the measuring chamber is reduced to negligible proportions. This enhances the safety of the apparatus because it may help to avoid undesirable heating of surfaces in contact with the environment or atmosphere of interest. Further, the interpretation of a change of signal caused by combustion is simpler if there is no significant temperature rise to be accounted for.

Combustion of a mixture of reactive components within the measuring chamber, or receiving volume, must not initiate combustion in the atmosphere of interest. For this purpose, at least one intervening means (termed "flame arrestors" herein) is positioned between the measuring chamber, or receiving volume, and the environment or atmosphere of interest. Suitable flame arrestors in the case of gaseous components may be formed by a diffusion barrier on the type known in the art, e.g. a sintered body such as a sintered plate, preferably consisting of a sintered inorganic material, e.g. a metal, such as sintered steel, or a sintered ceramic.

Alternatively, or complementally, the at least one flame arrestor may be formed by a conventional closure means, such as a valve, considered to be a "static" flame arrestor. Further, a membrane of the type specified in the above mentioned U.S. Pat. Nos. 4,906,333, 4,985,130 and 4,563,249 may be provided between the environment or atmosphere of interest and the receiving space. Such membranes are termed "semi-permeable" because they are capable of separating a normally liquid substance from a normally gaseous substance and are required if measurement is effected according to the pulsing method disclosed in U.S. Pat. Nos. 5,144,831 and 5,255,553, the disclosure of both of which is incorporated herein by way of reference. The membrane can be incorporated into the flame arrestor or be arranged separate therefrom in a manner preventing damage by combustion within the measuring chamber or receiving space.

Depending upon the choice of a "dynamic" flame arrestor in the sense of permitting continuous passage of gas from the atmosphere of interest into the measuring chamber, or receiving volume, as is the case when using a diffusion barrier, or a "static" flame arrestor, such as a valve, which permits interruption of the passage of the components of the environment of interest into the measuring chamber or receiving space, sampling will be continuous or discontinuous. With discontinuous sampling, control of the static flame arrestor can be effected advantageously by the control unit which may also control ignition time and sensor operation. Suitable control units are available commercially or may be built from commercially available elements.

A preferred type of ignition means is a heated wire or an electrical discharge device of the type forming an arc in the manner of spark plugs used for internal combustion engines. Such ignition means as well as their operation is well known in the art of combustion engines and needs no specific explanation.

The at least one sensor can be a conventional device for measuring the specific parameter, generally a parameter that is capable of indicating a composition, and can be selected in view of commercial availability and specific operative requirements. Commercially available sensors capable of measuring a thermal conductivity, or a pressure, of a combustible mixture in the measuring chamber, are mentioned by way of example but are not limiting. Obviously, relatively small sensors will be preferred in view of the small volume of the measuring chamber or of the receiving volume. More than one sensor could be used, in or connected with, the measuring chamber, and the same or different parameters could be measured by two or more sensors. By the same token, operation cycles could be the same or different if more than one sensor is used. Use of a thermal conductivity sensor is preferred for many applications of the invention, notably when measurement is made according to the pulsing method mentioned above.

Both apparatus and method according to the invention are suitable either for measuring the concentration or an oxidizable and preferably gaseous component, such as hydrogen or low molecular hydrocarbons, as the critical first gaseous component in an environment or atmosphere containing or receiving an oxidizing and preferably gaseous component, such as elemental oxygen or air, as the second reactive component; alternatively, both method and apparatus according to the invention could be used for measuring the concentration of an oxidizing component as the critical first component in an environment or atmosphere containing or receiving an oxidizable reactive component, such as hydrogen or a low molecular hydrocarbon, as the second component if monitoring of the oxidizing component by conventional methods such as amperometry, should present problems.

Generally, the invention is based on an interpretation of the chance of a signal generated by the at least one sensor caused when ignition causes combustion within the measuring chamber, or receiving space. This will be explained in more detail as applied to the specific case of an atmosphere containing elemental hydrogen ($H_2$) but similar considerations would apply to other environments or atmospheres. Again, sensors based on the measurement of thermal conductivity art of pressure are used for exemplification but other detection principles would be equally applicable in conjunction with the invention.

BRIEF DESCRIPTION OF THE DRAWINGS

The invention will be explained by way of illustration but not limitation with reference to the attached drawings in which:

FIG. 1 is a schematic cross sectional view of a first embodiment of an apparatus according to the invention;

FIG. 2 is a schematic cross sectional view of a second embodiment of an apparatus according to the invention;

DETAILED EXPLANATION OF THE DRAWINGS

Figure 3:
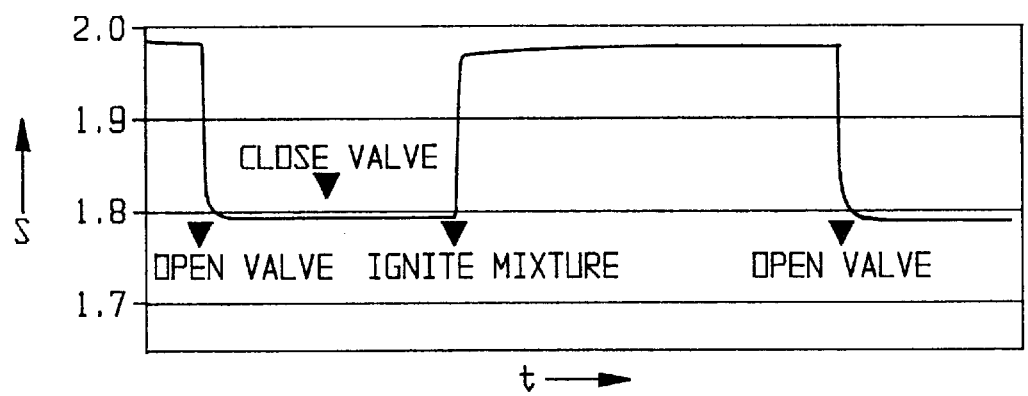
FIG. 3 is a diagram illustrating an example of a cycle when operating the method according to the invention.

FIG. 1 is a diagrammatic illustration of an apparatus 1 according to the invention connected via a conduit 102 with an environment E, e.g. the atmosphere contained in an enclosed space (not shown) potentially or effectively containing a gas, e.g. hydrogen, that would form a combustible mixture with the oxygen that is normally present within or outside of an enclosed space which is of analytical interest because it requires continuous monitoring.

Reaction chamber 12 is provided with flame arrestor in the form of a valve 14 operated by a solenoid 11 via valve stem 141. When the solenoid pushes the valve stem downwards, chamber 12 (the reaction volume) is filled with gas entering at the entrance port 102. Valve movement is controlled to avoid touching the ignition means which in this embodiment is a heating filament 135. Normally a pump and an exit port (not shown) are provided to assist the rapid exchange of gas in the reaction volume. Chamber 12 is sealed when the valve stem is retracted. Ignition means 135 and detection means 15 are sealed through plate 105 which closes chamber 12 and is held in place by a collar 104. Operation of solenoid 11 is controlled by a signal or signal sequence $A_2$ from control unit 16 indicated in FIG. 1 as a dash-dotted line. Also, control unit 16 triggers. ignition means 135 so that ignition is effected when valve 14 is closed. Control unit 16 is operatively connected with evaluation unit 17 for proper timing of the signals, or signal sequences before and after ignition, and for producing the signal, or signal sequence S that is indicative of the concentration of, for example, hydrogen, in environment E.

The materials of the constituents of apparatus 1 can be chosen to suit the application; typically, stainless steel could be used for enclosure of surrounding chamber 12 and for flame arrestor 14; sealing plate 105 preferably is made of an insulating material, such as a ceramic, while gasket 103 would be of an elastomeric material, such as rubber.

Detection means 15 then produces an initial signal characteristic of the composition of the unreacted combustible gas mixture. Although the choice of the type of detection means used is not an essential part of the invention and can be selected by those experienced in the art in view of the specifics of the monitoring system required, a schematic example given by way of illustration is depicted in FIG. 1 as a simple resistance wire 15, warmed by an electric current supplied via conduits 151,152 and eposited on sealing plate 105.

The temperature, and hence the resistance, attained by this wire depends upon the thermal conductivity of the gas; accordingly, the voltage developed across it by the electric current could be used as a measure of the gas composition.

Heating ignition wire 135 to a high temperature (~1000° C.) with an electric current supplied through contacts 131, 132 causes the gas mixture to burn so that the combustible component as well as some oxygen (or another oxidizing agent) is removed and forms a product of the combustion reaction. The change in the signal from detection means 15 can then be interpreted to give information about the concentration of the combustible component in the original mixture.

The graph illustrated in FIG. 3 presents the result of one experiment in which a 30%$H_2$/Air mixture was repeatedly introduced into the reaction chamber, and ignited. The ordinate shows the signal strength S, e.g. in Volts (V) from the detector. The abscissa indicates time (t) during a cycle from "open valve", "close valve", and "ignite mixture" to the next cycle beginning with "open valve". A typical cycle time in FIG. 3 would be a period of 10 seconds.

The temperature changes a little as a consequence of the combustion, and the signal changes during about 10 seconds following ignition as the system returns to the ambient temperature.

Figure 4:
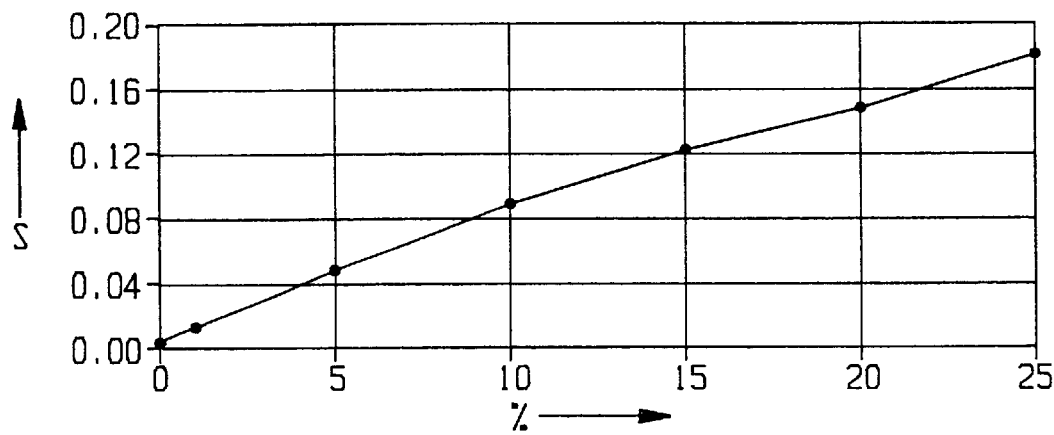
FIG. 4 is a diagram illustrating signal strength as a function of concentration of a critical first component when operating an embodiment of the inventive method.

In practice, a calibration curve can be constructed, recording the variation of signal voltage as a function of the fraction of the combustible gas in the mixture under study. This curve can then be consulted during analysis of an unknown mixture to determine the concentration from the observed signal voltage change. The diagram shown in FIG. 4 presents the result of such a test. The ordinate indicates the change of the signal S upon ignition while the abscissa indicates the concentration of hydrogen in percent (%)

The embodiment of the apparatus according to the invention illustrated in FIG. 1 above incorporates, as flame arrestor, an isolation valve actuated by a solenoid, which can impose limitations on the environmental conditions or working life of the sensor. Replacement of the valve by a sintered steel (or equivalent) flame barrier between environment E to be monitored and the measuring chamber 22 as receiving volume is illustrated in FIG. 2 and retains the advantages of the means of entry into the volume of the atmosphere to be monitored and of the exit of the products of the reaction out of the volume, of the extinguishing of flame propagation, while also eliminating moving parts. It should be noted that the reference numerals in FIG. 2 correspond with those of FIG. 1 except for the first digit which corresponds with the number of the figure. Accordingly, elements with corresponding numerals in FIG. 2 are substantially the same as those in FIG. 1 so that no additional explanation is needed for FIG. 2.

Apparatus 2 shown in FIG. 2 for preferred continuous operation provides for flame arresting characteristics equivalent to those of a valve by means of a diffusion barrier 24 of sufficient mechanical stability, such as "sinter", e.g. a body or plate made of sintered steel, which can sufficiently impede entry of hydrogen into measuring chamber 22 for the short duration of the combustion reaction. In quantitative terms, the apparatus illustrated in FIG. 2 is characterized by two potentially rate-determining steps: the rate of the combustion reaction, and the rate of passage of gas molecules from environment E into the measuring chamber 22, i.e. into the receiving space or reaction volume, through the sinter. Provided the rate of the combustion exceeds that of the permeation by a substantial factor, at least five or preferably 20 times, then the behavior of this simpler apparatus of FIG. 2 will emulate that of the apparatus of FIG. 1, and a similar quantitative interpretation of the results can be used. Generally, the diffusion-limiting capacity of the flame arrestor can also be provided by a "semipermeable" membrane as explained in more detail below.

Thus a steady state signal can be observed at 27 for a sufficiently long duration following ignition to permit measurement results which are characteristic of the products of the combustion. The difference between this and the signal before ignition can then be used to calculate the fraction of the combustible component in the atmosphere.

If this required inequality of the rate constants is not observed, a dynamic model of the system needs to be employed to analyze the time dependence of the signal from the detector.

Figure 5:
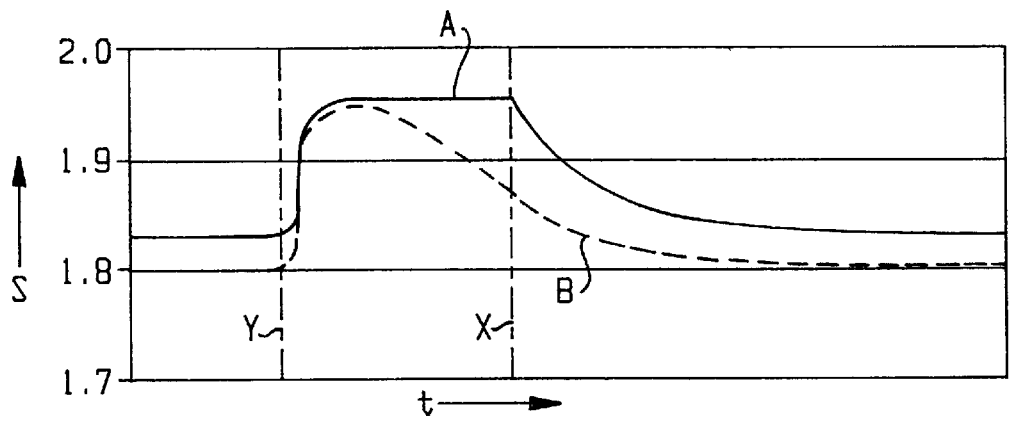
FIG. 5 is a diagram illustrating signal curves for different concentrations of a critical first component when operating another embodiment of the inventive method.

The diagram shown in FIG. 5 represents the result of ignition of two different mixtures of $H_2$ in air. Again, the strength of the signal, e.g. in Volts, is shown on the ordinate while the abscissa indicates time (t), e.g. spanning a period of about 20 seconds. Point Y indicates the moment of ignition while point X indicates the moment of heating. In FIG. 5 point displaced. Curve A is for a mixture of 15%, by volume, of hydrogen, in air; curve B is for a mixture of 20%, by volume, of hydrogen in air. When only 15% of $H_2$ are present (curve A), the rate of arrival of $H_2$ and $O_2$ into the burning mixture in the reaction volume by permeation through the sinter is insufficient to cause an observable change in the composition of the reaction products. In accordance with the explanation given above, a steady state is then observed, and the reaction products have a constant composition characterized by a constant signal from the detection means. The difference in the signals caused by the ignition can then be interpreted to yield the fraction of $H_2$ in the mixture.

When the $H_2$ concentration is raised to 20%, however, the arrival rate of $H_2$ is sufficient to gradually change the composition of the reaction products resulting in a falling signal. This state of affairs can be countered by reducing the permeability of the sinter.

Figure 6:
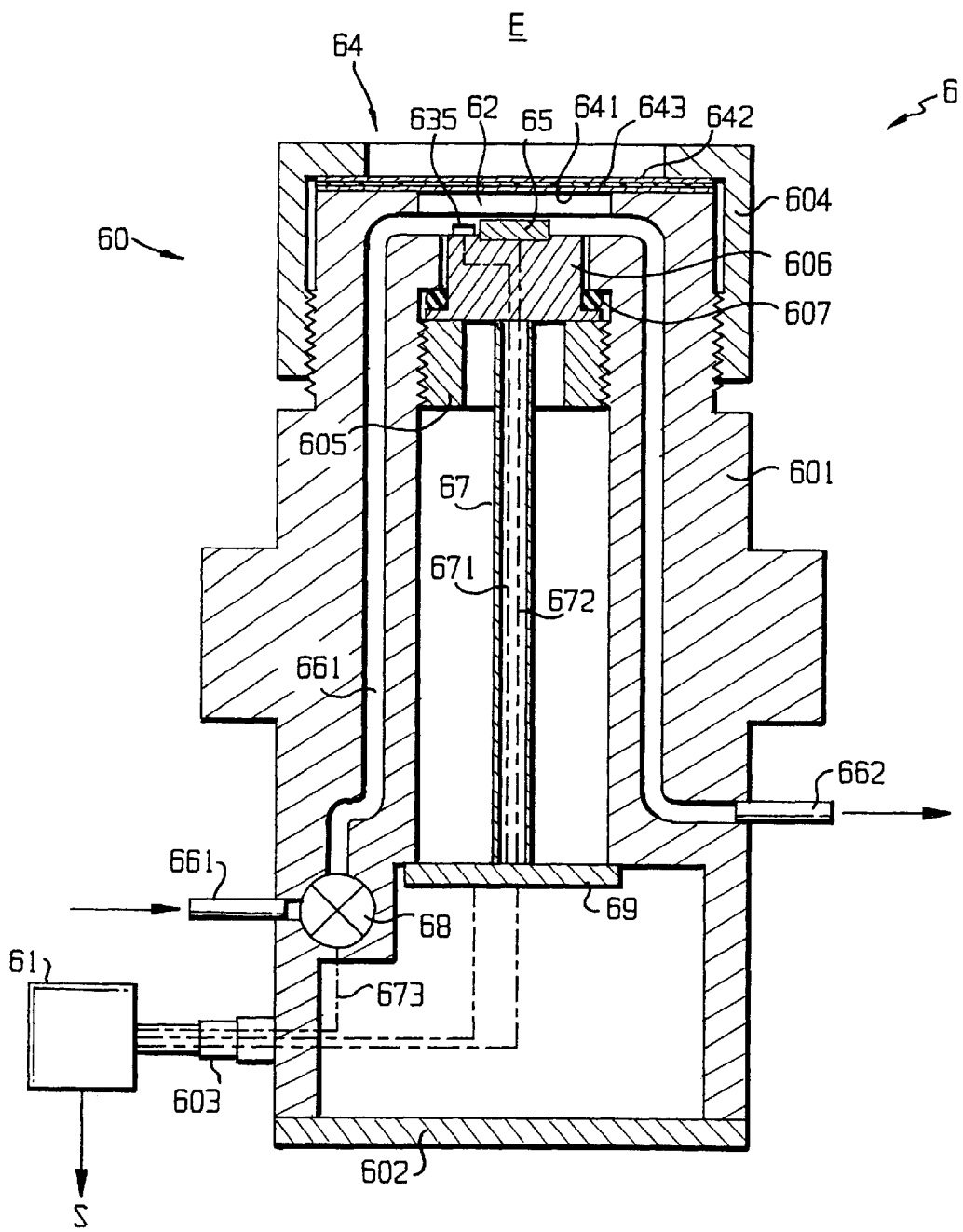
FIG. 6 is a schematic cross sectional view of a third embodiment of an apparatus according to the invention for measuring by means of a pulsing method of operation.

Apparatus 6 shown in diagrammatic cross section in FIG. 6 resembles the apparatus if FIG. 2 of U.S. Pat. No. 5,255,553 for use with the pulsing monitoring mode except that, according to the teachings of the present invention, an ignition means 635 connected with control unit 661 is provided and that membrane 643 is sandwiched between two metal screens 641,642 or similar permeable supports together forming flame arrestor 64. Membrane 643 is permeable for the known gaseous components of the atmosphere of interest (environment E) but is substantially impermeable for liquids. Supports 641,642, on the other hand, are selected for stability of arrestor 64 and should not interfere significantly with the passage of gaseous components from environment E into chamber 62 because membrane 643 acts as a diffusion control. It should be emphasized that the receiving volume of chamber 62 as illustrated in FIG. 6 is depicted with an exaggerated volume for illustration purposes only.

Apparatus 6 of FIG. 6 includes a sampling unit or probe 60 formed by a generally cylindrical casing 601, a bottom closure 602, and a screwed-on holding ring 604 which keeps arrestor 64 in a sealing connection with casing 601. Measuring chamber 62 includes a sensor 65, typically a thermo-conductivity sensor, and an ignition means 635, typically in the form of a platinum wire which can be heated to an ignition temperature by means of an electrical supply 671 which, together with connecting line 672 of sensor 65, is passed through a tubular guide 67 to plate 69 which may include a printed wire board for signal processing.

Chamber closure 606 is held by a screwed-in insert 605 and a sealing ring 607 in sealed connection with casing 601. Conduits duits 661,662 are provided for passing a flushing gas, typically air, from a source of pressure or suction (neither shown in FIG. 6) into chamber 62. Conduit 661 is shown to comprise a valve 68 with an electrical actuator line 673 for controlling flushing of chamber 62. However, control valve 68 might be arranged in conduit 662, or each conduit could be provided with a control valve of its own.

Control of operation including timing of flushing, accumulation, ignition and any other phases of operation can be combined with signal processing and signal evaluation by computing means in an integral unit 61 to generate signal S.

Alternatively, operation control and signal processing can be effected in separate control and computation means.

A preferred method of cyclically operating an analyzer of the type shown in FIG. 6 is as follows:
  (i) in a first phase of each cycle, chamber 62 is purged with air via conduits 661,662 and thermal conductivity of this air charge is measured to give a first signal or signal sequence;
  (ii) after closing control valve 68, accumulation of combustible and interfering gases from environment E passing by diffusion through membrane 643 into chamber 62 is permitted during a second phase of each cycle to produce a second signal or signal sequence at or near the end of the accumulation period;
  (iii) a third phase of each cycle starts with igniting the gases contained in chamber 62 by actuating ignition 635 to generate a third signal or signal sequence which is characteristic of the products of the combustion reaction.

By means of the computations explained mathematically below, signal (S) is computed from:
  an interpretation or evaluation of the difference between the signals or signal sequences emitted by thermal conductivity sensor 65 during the second and third phase to produce a measure of the partial pressure of the combustible gas, and
  an interpretation or evaluation of the difference between the signals or signal sequences emitted by thermal conductivity sensor 65 during the first and second said phases to produce a measure of the partial pressure of the interfering gas.

Optionally, each measuring cycle may include an additional or fourth intermediate phase for permitting dissipation of heat generated by ignition and computing a correction for use in computing signal S.

The following examples are given to illustrate operation of the inventive method including mathematical treatment of the parameters of measurement.

EXAMPLE 1

The apparatus used was essentially as explained in FIG. 1. Sensor 15 was a conventional monolithic miniature solid-state thermal conductivity detector (Hartmann & Braun, Germany) for measuring thermal conductivity of a gas mixture.

The atmosphere of interest consisted of $H_2$, $O_2$, $N_2$, water vapor, and impurities, enclosed in a small volume V. The thermal conductivity is represented by $\lambda$ which may be expressed, to a good approximation, as a linear combination of terms containing products of the mole fractions $x_j$ and the thermal conductivities $\lambda_j$ of each of the components:

$$\lambda = x_H \lambda_H + x_O \lambda_O + x_N \lambda_N + x_W \lambda_W + x_I \lambda_I$$

Now, the mixture is ignited so that all of the $H_2$ burns in the excess of $O_2$:

$$2H_2 + O_2 = 2H_2O$$

and the thermal conductivity is measured again:

$$\lambda^1 = x_O^1 \lambda_O^1 + x_N^1 \lambda_N^1 + x_W^1 \lambda_W^1 + x_I^1 \lambda_I^1$$

It will be appreciated that the thermal conductivities of the components ($\lambda^1_H$ etc.) may have changed from their values before the ignition ($\lambda_H$ etc.) because of temperature change. The relations between the mole fractions before and after the ignition can be expressed as follows:

$$x_N^1 = x_N/(1 - x_H/2)$$

$$x_I^1 = x_I/(1 - x_H/2)$$

$$x_O^1 = \frac{OH}{1 - x_H/2}$$

$$x_W^1 = \frac{WH}{1 - x_H/2}$$

Assuming there is a delay to allow the heat released by the ignition to dissipate so that the temperatures and the thermal conductivities of the components return to the values they had before the ignition ($\lambda_H^1 = \lambda_H$ etc. the thermal conductivity of the mixture resulting from the ignition can be expressed by:

$$\lambda^1 = [1/(1-x_H/2)]*(\lambda - x_H*\lambda_H) + [x_H/(1-x_H/2)]*(\lambda_W - \lambda_O/2)$$

or $$\lambda^1*(1-x_H/2) = \lambda + x_H*[\lambda_W - \lambda_H - \lambda_O/2]$$

This form of the mathematical expression is particularly convenient because it contains only one composition dependent term, $x_H$, which can therefore be isolated explicitly:

$$x_H = \frac{\lambda^1 - \lambda}{\lambda^1/2 + \lambda_W - \lambda_H - \lambda_O/2} = \frac{\lambda^1 - \lambda}{\lambda^1/2 - a}$$

where $$a = \lambda_H + \lambda_O/2 - \lambda_W$$

Provided that a (or $\lambda_O$, $\lambda_W$, and $\lambda_H$) is known, and $\lambda$ and $\lambda^1$ are measured, the mole fraction of $H_2$ in the atmosphere can be calculated. The value of a can be found by a calibration procedure using an atmosphere of known composition.

EXAMPLE 2

Another embodiment of the method according to the invention is carried out by measuring pressures and temperatures before (P, T) and after ($P^1$, $T^1$) ignition. Assuming that the atmosphere of interest behaves substantially as an ideal gas, the ratio of the total number of moles of gas before ignition to that after ignition is $$\frac{1}{1 - x_H/2} = \frac{PV/T}{P^1 V^1/T^1}$$

From this expression the parameter $X_H$ can be recovered to give an explicit relation for the mole fraction of $H_2$. Temperature variations due to ignition are accounted for in this equation, but again, the interpretation is simplified if the temperature and volume variations are negligible. This mathematical analysis is appropriate for a steady state system in which the quantity of gas enclosed in the receiving volume is constant as is the case with an apparatus according to FIG. 1. When using an apparatus of the type illustrated in FIG. 2 where the flame arrestor 24 is a sintered steel plate, continuous diffusion of the atmosphere to be monitored into the receiving volume occurs during the ignition period, so feeding more fuel to the burning mixture. It is unlikely that all components of the mixture would diffuse equally rapidly through the sinter, so that the gas composition emerging into the receiving volume could have a different composition from that in the original atmosphere. This would cause the signal from the detector to vary in time (a dynamic technique) following the ignition, but in principle, the shape of the signal versus time envelope still contains information about the composition of the atmosphere to be monitored.

EXAMPLE 3

Analysis of the Waste Gases Issuing from a Nuclear Reactors

As is well known in the art of operating nuclear reactors, it is essential that, prior to releasing the gases from within the reactor into the environment, hydrogen is removed by a recombination device or "recombiner" by catalytic reaction with a stoichiometrically equivalent amount of oxygen.

In prior art practice, the presence of helium interferes with the determination of the quantity of elemental hydrogen in the gas mixture by standard analyzers based upon measuring thermal conductivity. However, application of the embodiment of the invention according to this example allows determination of the partial pressure of elemental hydrogen from the change of thermal conductivity during the combustion period, when the hydrogen burns to water, and if desired, the partial pressure of helium from the combination of this result with the rate of change of thermal conductivity signal during the accumulation phase.

To this end an apparatus of the type shown in FIG. 6 was used in combination with the pulsing method disclosed in U.S. Pat. Nos. 5,144,831 and 5,255,553 with particular reference to FIGS. 7 and 8 of the present drawings.

The atmosphere issuing from standard nuclear reactors (as environment E of this example) is known to consist of hydrogen, helium and nitrogen. The thermal conductivity of nitrogen is sufficiently close to that of the purge gas (air) so that nitrogen is not an interfering component. Helium, on the other hand, has a thermal conductivity substantially different from that of the purge gas and, thus, interferes with determination of the partial pressure of hydrogen which, in turn, has a thermal conductivity substantially different from that of air (purge gas) and nitrogen.

In other words, the expressions "interference" or "interfering component" used in the context of the present invention are relative terms; in fact, this embodiment of the inventive method can be used for determination of the partial pressure of hydrogen, and/or or for determination of the partial pressure of helium in a gas mixture containing these two components plus any further component(s) which—as in the case of nitrogen—has or have a thermal conductivity close to that of the purge gas (air) and presents no interference.

In this mode of operation, thermal conductivity detector 65 produces a signal or signal sequence characteristic of the composition of the gas mixture contained in reaction chamber 62, isolated from the sample or environment E to be measured by flame arrestor 64 including membrane 643. Measurements are taken periodically in a virtually endless series of identical cycles controlled by a microprocessor arranged, for example within control unit 61, each cycle comprising a purging phase, an accumulation phase and a combustion phase.

Figure 7:
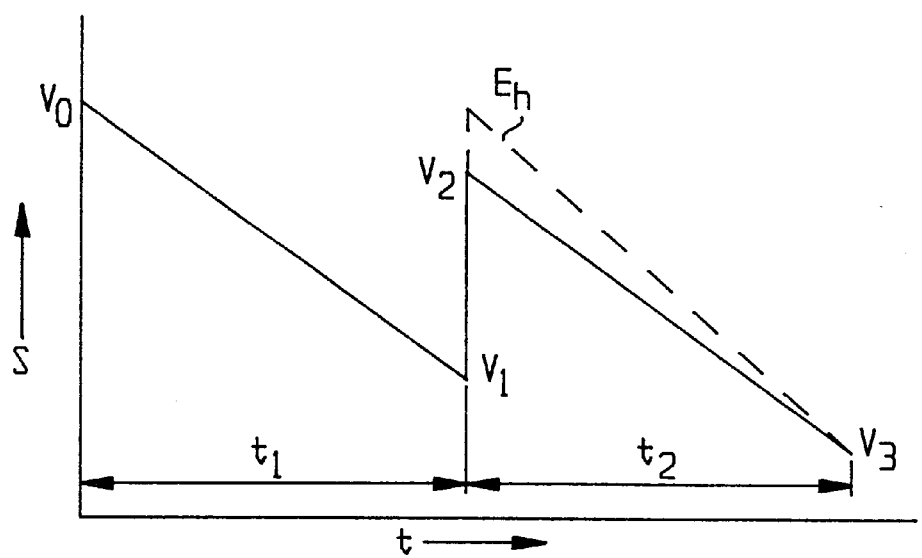
FIG. 7 is a diagram illustrating signal evolution when measuring by means of a pulsing method using a flushing gas.

FIG. 7 illustrates signal evolution during each cycle of measurement; time t is shown on the abscissa. The strength of signal S is shown on the ordinate, e.g. in terms of voltage, starting at $V_0$ and dropping, during a first period $t_1$ to $V_1$ which is the signal strength at the moment of ignition $M_i$. As a consequence of ignition, the signal rises to a value $V_2$. As indicated by dotted line $E_h$ the actual signal obtained upon ignition is increased by the effect of heat generated when operating filament 635 to initiate combustion; this heat is dissipated, however, at the end of the second accumulation period $t_2$ when signal strength has dropped to $V_3$.

During the purging phase of each cycle, electrically controlled valve 68 is opened to allow air to flush chamber 62 via conduits 661,662 in order to obtain a background signal from thermal conductivity detector 635 characteristic of pure air. Purging with air also provides an excess of oxygen for burning hydrogen as the combustible component during the subsequent combustion phase.

At the start of period $t_1$, electrically controlled valve 68 is closed and gases diffuse through membrane 643 from the medium or environment E to be analyzed into chamber 62 mixing with the air remaining from the purge. The rate of change, or slope, of the thermal conductivity signal S is as follows:

$$S=(k_1P_1+k_2P_2)$$

in which $k_1$ and $k_2$ are constants while $P_1$ and $P_2$ are the partial pressures of the combustible gas (hydrogen) and of the interfering gas (helium).

Magnitude and temperature dependence of constant $k_1$ can be determined by analyzing the rate of change of the signal throughout the temperature range of interest, due to a known constant pressure of the combustible gas in the absence of the interfering gas ($P_2=0$); $k_2$ results from a similar procedure in the absence of the combustible gas ($P_1=0$).

Platinum filament 635 is heated initiate combustion of the gas mixture which has accumulated in chamber 62 by diffusion from environment E through membrane 643. Combustion is prevented from spreading into environment to be monitored by flame arrestor 64 including membrane 643 sandwiched between and supported by its metallic supports in the form of screens or sinter plates 641,642. When operating according to the inventive method, the change of the thermal conductivity signal $\delta V$ as a result of the combustion will be linear and uniquely correlated with the partial pressure of the combustible component in environment E which is to be monitored:

$$\delta V=a+b*P_1$$

thus providing for measurement of $P_1$ from the change of $\delta V$. This is due to the fact that the change of the gas composition within chamber 62 caused by removal of some oxygen by reaction with the combustible component—hydrogen—and formation of combustion product (water) may be expressed directly in terms of the original partial pressure of the first component.

A factor to be considered when measuring $\delta V$ is the effect of the heat generated by filament 635 on the thermal conductivity signal. This can be compensated by measuring the signal at the end of a further accumulation period chosen to be long enough to permit this spurious heat to dissipate. Assuming that the rate of change of the signal during this period is the same as during the first accumulation period, were it not for the heating effect, quantity $\delta V$ can then be calculated.

A calibration curve is established by measuring the magnitude of this change in gas mixtures of known composition so that constants a and b can be determined. Again, a temperature dependence of parameters a and b can be quantified by analyzing the temperature range of interest.

The calibration curve obtained is used to calculate the partial pressure of the combustible component in the atmosphere E of interest when measuring its content of the first component. This result is combined with the rate of change of the thermal conductivity signal during the accumulation period and the partial pressure of interfering gas may also be calculated.

In the practice of this embodiment of the invention, the rate of change of signal during the first accumulation period is linear in time while the rate of change of signal S is as follows:

$$S=(V_0-V_1)/t_1=-(k_1{}^*P_1+k_2{}^* P_2)$$

The signal after combustion $V_2$ (and therefore the signal jump $\delta V$) can be calculated as follows:

$$\delta V=V_2-V_1=V_3+S{}^*t_2-V_1=a+b\, P_1$$

Hence:

$$P_1=(V_3-V_1+t_2{}^*(V_0-V_1)/t_1)/b-a$$

and $$P_2=-\{(V_0-V_1)/t_1+k_1{}^*P_1\}/k_2$$

Temperature should also be measured for correction or normalization and appropriate values are calculated for constants k1, k2, a, and b at the actual temperature of operation.

Figure 8:
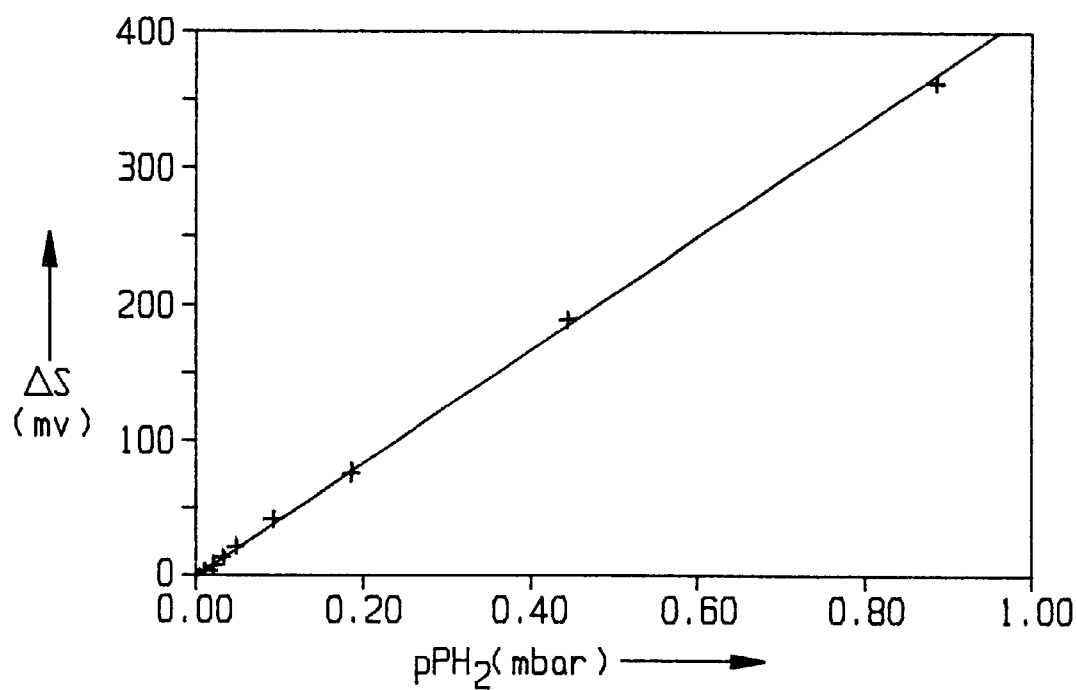
FIG. 8 is a diagram showing signal change when monitoring hydrogen in relation to its partial pressure in an atmosphere containing nitrogen and helium as additional components.

To demonstrate the validity of this approach, a series of gas mixtures of known composition (at a constant temperature of 30° C. and a pressure 970 mbar) was prepared containing from Zero to 90% by volume of $H_2$, 10% by volume of He, and from Zero to 90% by volume of $N_2$. These mixtures were analyzed as described and the results are illustrated in FIG. 8 which shows the dependence of the signals obtained upon the percentage of H2 in the gas mixtures. The straight line of least squares through the measuring points obtained by the experiment is expressed by the following equation:

$$\text{Signal}=\delta V=a+bP_1$$

where a=4.022 mV and b=410.8 mV/bar. In this manner, the partial pressures of $H_2$ and He within the nuclear reactor were measured and monitored according to the invention.

Generally, the inventive apparatus and method are capable of analyzing hazardous or potentially hazardous atmospheres with adequate accuracy within the range of concentrations of interest. The interpretation based on the change of properties of the atmosphere caused by the ignition (a differential technique), rather than on absolute measurements, is capable of producing results independent of interference by other components. The interposition of at least one flame arrestor between the atmosphere of interest and the measuring chamber excludes the risk of ignition of the gas mixture by heated or catalytically active surfaces. The incorporation of two or more independent, e.g. distanced, flame arrestors rather than only one can be desirable if safety of operation is to be increased.

It should be noted that the specific type of parameter of the gas mixture in the measuring chamber or in the receiving volume is not believed to be overly critical and the examples given above are preferred for many uses because of their linear additive contributions of the components in the atmosphere of interest but are by no means understood as a limitation. In other words, one and the same property should be measured before and after ignition of the mixture of components such that the combustion reaction has proceeded to completion and thermal conductivity is the preferred property for many applications of the invention.

It will be apparent from the above disclosure that the invention provides for inexpensive, interference free method of determining the partial pressure of a combustible component in a gas mixture containing two or more components, suitable for continuous, unattended, in-line monitoring. Various modifications of the above will be apparent to those experienced in the art. The scope of the invention is to be construed from the following claims.

What is claimed is:

1. An apparatus for determining the concentration of a critical first component of an environment, said first component being capable of forming a combustible mixture with a second component; said apparatus comprising:

(A) a sampling unit including:
(A1) a measuring chamber operatively connected with an ignition means capable of being operated so as to initiate in said chamber a combustion of said critical first component by reaction with said second component, and
(A2) at least one sensor operatively connected with said measuring chamber for generating a signal formed by essentially proportionate contributions from all components contained in said measuring chamber, said at least one sensor being capable of measuring a thermal conductivity or a pressure of a gaseous mixture in said measuring chamber;

(B) at least one flame arrestor intervening between said measuring chamber and said environment of interest;

(C) a control unit capable of imposing a mode of operation in at least two distinct phases wherein, during a first phase, said environment of interest is allowed to accumulate in said measuring chamber; and wherein, during a second phase, said ignition means is operated for initiating said combustion in said chamber; and (D) a means for evaluating at least one first signal generated by said at least one sensor before operation of said ignition means, and at least one second signal generated by said at least one sensor after operation of said ignition means, said at least one second signal being a steady state signal, and for generating, from said at least one first signal and said at least one second signal, a signal which depends on said at least one first signal and said at least one second signal and is indicative of said concentration of said critical first component in said environment of interest.

2. The apparatus of claim 1, wherein said first and said second components are gaseous, said first component is hydrogen and second component is oxygen.

3. The apparatus of claim 1, wherein said at least one flame arrestor comprises a diffusion barrier arranged between said environment (E) and said measuring chamber.

4. The apparatus of claim 1, further comprising a semi-permeable membrane arranged between said environment (E) and said measuring chamber.

5. The apparatus of claim 1, wherein said at least one sensor is capable of measuring thermal conductivity.

6. The apparatus of claim 1, wherein said control unit includes a first actuating control for said ignition means and, if said arrestor is a closure means, a second actuating control for said closure means.

7. The apparatus of claim 1, comprising means for passing a flushing gas containing said second component through said chamber and means for controlling such passage.

8. A method of determining the concentration of a critical first gaseous component of an environment capable of forming an explosive mixture with a second gaseous component; said method comprising the steps of:

(a) providing a receiving volume in operative connection with an ignition means capable of initiating explosive combustion in said receiving volume of a mixture containing said critical first component and said second component;

(b) providing flame arrestor means between said receiving volume and said environment;

(c) permitting, during a sampling phase, a portion of said environment to enter into said receiving volume in a continuous or discontinuous manner;

(d) providing at least one sensor in operative connection with said receiving volume so as to generate signals formed by essentially proportionate contributions from all components contained in said receiving volume, said at least one sensor being capable of measuring a thermal conductivity or a pressure of a gaseous mixture in said receiving volume;

(e) operating said ignition means so as initiate combustion of said mixture in said receiving volume;

(f) obtaining from said at least one sensor at least one first signal before, and at least one second signal after, operating said ignition means, said at least one second signal being a steady state signal; and (g) processing said at least one first signal and said at least one second signal obtained before and after operation of said ignition means to generate, from said at least one first signal and said at least one second signal, a signal which depends on said at least one first signal and said at least one second signal and is indicative of said concentration of said critical first component in said environment of interest.

9. The method of claim 8, wherein said first component is hydrogen and said second component is oxygen.

10. The method of claim 8, wherein a flushing gas containing said second component is passed through said chamber prior to said sampling phase.

11. The method of claim 8 further including the step of imposing a mode of operation in at least three distinct phases wherein, during a first phase, said chamber is flushed with a gas containing said second component; during a second phase said environment is allowed to accumulate in said chamber; and during a third phase said ignition means is operated.

12. The method of claim 11 wherein said mode operation includes a fourth phase for temperature equilibration after ignition.

13. The method of claim 8, wherein said sensor is capable of measuring thermal conductivity.

14. The method of claim 8, wherein each operation of said ignition is coordinated with said obtaining of said signals to constitute a cycle comprising one operation of said ignition, at least one signal before ignition, and at least one signal after ignition; and performing a sequence of such cycles.

15. The method of claim 14 wherein each cycle includes a phase of flushing said receiving volume with a gas which is free of said first component.

16. The method of claim 15 wherein said flushing gas contains said second component.

17. The method of claim 8, for measuring the concentration of an oxidizable gas, such as hydrogen or a low molecular hydrocarbon, as said critical first gaseous component comprising combusting said oxidizable gas in the presence of an oxidizing gas, as said second gaseous component in an amount sufficient, at least for stoichiometric reaction with said critical first component.

18. The method of claim 8 wherein said sampling unit comprises a membrane permeable for gases and arranged between said chamber (62) and said atmosphere or environment to be monitored, said chamber including: a means (661,662) of purging the said chamber with air, a thermal conductivity sensor (65) which produces a signal (S) characteristic of the composition of the gas mixture contained within said chamber at any moment, and at least one means (635) of ignition of the gases contained within the chamber, said method including at least three phases of operation under the control of an electronic control unit (661), wherein:

(i) a first phase for purging said chamber with air and permitting measurement of thermal conductivity of said air to give a first signal;

(ii) a second phase for permitting accumulation of combustible and interfering gases from said environment in said chamber by diffusion through said membrane and producing a second signal at the end of the accumulation period; and (iii) a third phase for igniting the gases contained in said chamber at the end of said accumulation period and generating a third signal which is characteristic of the reaction products, said signal (S) being computed essentially from an evaluation of the difference between the signals emitted by said thermal conductivity sensor during said second and third phase to produce a measure of the partial pressure of the combustible gas, and an evaluation of the difference between the signals emitted by said thermal conductivity sensor during the first and second said phases to produce a measure of the partial pressure of the interfering gas.

19. The method of claim 18 comprising a fourth phase for permitting dissipation of heat generated by said ignition, and computing a correction for use in computing said signal (S).

20. The apparatus of claim 1, wherein said measuring chamber has a volume of less than 1 ml.

21. The method of claim 8, wherein the receiving volume has a volume of less than 1 ml.

\* \* \* \* \*